United States Patent
Colpas et al.

(10) Patent No.: US 8,377,651 B2
(45) Date of Patent: Feb. 19, 2013

(54) **METHOD FOR DETECTING *ESCHERICHIA COLI***

(75) Inventors: Gerard J. Colpas, Holden, MA (US); Diane Ellis-Busby, Lancaster, MA (US); Shite Sebastian, Somerville, MA (US); Mitchell C. Sanders, West Boylston, MA (US)

(73) Assignee: Systagenix Wound Management (US), Inc. (GB)

( * ) Notice: Subject to any disclaimer, the term of this patent is extended or adjusted under 35 U.S.C. 154(b) by 0 days.

(21) Appl. No.: 12/894,212

(22) Filed: Sep. 30, 2010

(65) Prior Publication Data

US 2011/0070594 A1 Mar. 24, 2011

Related U.S. Application Data

(62) Division of application No. 10/543,554, filed as application No. PCT/US2004/002594 on Jan. 30, 2004, now abandoned.

(60) Provisional application No. 60/444,523, filed on Jan. 31, 2003.

(51) Int. Cl.
*C12Q 1/37* (2006.01)
(52) U.S. Cl. .............................. 435/23; 435/7.32; 435/41
(58) Field of Classification Search ................... 435/23, 435/7.32, 41
See application file for complete search history.

(56) References Cited

FOREIGN PATENT DOCUMENTS

EP    0428000 A1 *  5/1991

OTHER PUBLICATIONS

Schmidtchen et al. "Proteinases of common pathogenic bacteria degrade and inactivate the antibacterial peptide LL-37", Molecular Microbiology, 2002, 46(1):157-168.*
Otto et al. "Characterization of a hemoglobin protease secreted by the pathogenic *Escherichia coli* strain EB1", J. Exp. Med., 1998, 188(6):1091-1103.*
Rimmele et al. "Trehalose-6-phosphate hydrolase of *Escherichia coli*", J of Bacteriology, 1994, 176(18):5654-5664.*

* cited by examiner

*Primary Examiner* — Susan Hanley
*Assistant Examiner* — Bin Shen
(74) *Attorney, Agent, or Firm* — Stephen B. Salai, Esq.; Jodi A. Reyonlds, Esq.; Harter Secrest & Emery LLP

(57) ABSTRACT

Described herein are methods of detecting an infection and for detecting the presence or absence of microorganisms, for example, wound pathogens in a sample, by contacting a sample with an enzyme produced and/or secreted by the bacteria, and detecting modification or the absence of modification of the substrate, as an indicator of the presence or absence of the enzyme in the sample. The present invention also features a biosensor for detecting the presence or absence of bacteria in a sample.

7 Claims, 5 Drawing Sheets

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Asp Ser Arg Pro Val Arg Arg Arg Arg Pro Arg Val Ser Lys
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Lys Val Ser Arg Arg Arg Arg Arg Tyr Tyr Asp
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

Lys Lys Ala Ser Glu
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 4

Val Ser Arg Arg Arg Arg Arg Gly Gly Lys
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide
```

```
<400> SEQUENCE: 5

Cys His His His Ala Ser Glu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Val Ser Arg Arg Arg Arg Arg Gly Gly Lys
1               5                   10
```

METHOD FOR DETECTING *ESCHERICHIA COLI*

RELATED APPLICATIONS

The present application is a divisional of U.S. application Ser. No. 10/543,554, filed 28 Apr. 2006 ABN, which is a U.S. National Stage Entry of PCT/US2004/002594, filed Jan. 30, 2004, which claims Priority from U.S. Provisional Application Ser. No. 60/444,523, filed 31 Jan. 2003 (now expired), all of which are hereby incorporated by reference in their entireties.

BACKGROUND OF THE INVENTION

Infections are a major source of healthcare expenditure. Approximately 5% of all surgical wounds become infected with microorganisms, and that figure is considerably higher (10-20%) for patients undergoing abdominal surgery. Bacterial species, such as *Escherichia coli* (*E. coli*) are the most frequently isolated organisms from infected wounds. Bacterial colonization rates are significantly higher in the hospital setting, both among healthcare workers, and among patients. Moreover, the colonizing organisms in the hospital environment are likely, to be resistant to many forms of antimicrobial therapy, due to the strong selective pressure that exists in the nosocomial environment, where antibiotics are frequently used. Most strains of *Escherichia* call can harmlessly coexist with humans, for example, in their intestines, and are not likely to cause disease under normal circumstances. Some strains, however, produce toxins that can cause severe, even life threatening disorders, including intestinal disorders, kidney disorders, and urinary tract infections.

*Escherichia coli* are one type of pathogenic microorganism that can be found infections in the human body; others include, but are not limited to *Streptococcus pyogenes, Pseudomonas aeruginosa, Enterococcus faecalis, Proteus Serratia marcescens, Enterobacter clocae, Acetinobacter anitratus, Klebsiella pneumoniae*, and *Staphylococcus* species.

Infection, including wound infection due to any of the above organisms is a significant concern of hospitals. The most common way of preventing such infection is to administer prophylactic antibiotic drugs. While generally effective, this strategy has the unintended effect of breeding resistant strains of bacteria. The routine use of prophylactic antibiotics should be discouraged for the very reason that it encourages the growth of resistant strains.

Rather than using routine prophylaxis, a better approach is to practice good anti-microbial management, i.e., keep area at risk for becoming infected away from bacteria before, during, and after surgery, and carefully monitor the wound site or patient fluid for infection. Normal monitoring methods include close observation of the wound site for slow healing, signs of inflammation and pus, as well as measuring the patient's temperature for signs of fever and testing the patient's fluids, for example, urine, for signs of infection. Unfortunately, many symptoms are only evident after the infection is already established. Furthermore, after a patient is discharged from the hospital they become responsible for monitoring their own healthcare, and the symptoms of infection may not be evident to the unskilled patient.

A system or biosensor that can detect the early stages of infection before symptoms develop would be advantageous to both patients and healthcare workers. If a patient can accurately monitor the condition of a wound after discharge, then appropriate antimicrobial therapy can be initiated early enough to prevent a more serious infection.

SUMMARY OF THE INVENTION

It has been found that molecules, for example, proteins secreted by microorganisms, such as bacteria or fungi, expressed on the cell surface of microorganisms, or expressed on the surface of a cell infected with a virus or prion can serve as markers for the detection of the presence or absence of the microorganism in a sample, for example, a wound or body fluid. Accordingly, the present invention features a method of detecting the presence or absence of a microorganism, for example, *E. coli* in a sample by detecting the presence or absence of a molecular marker for the microorganism in the sample. In particular, the molecular markers to be detected include proteins, such as enzymes that are specific to a species of microorganism.

In one aspect, the invention features a method for detecting the presence or absence of a microorganism, for example, *E. coli* in a sample, comprising the steps of contacting the sample with a delectably labeled substrate for an enzyme produced and/or secreted by the microorganism, under conditions that result in modification of the substrate by the enzyme; and detecting the modification or the absence of the modification of the substrate. Modification of the substrate indicates the presence of the microorganism in the sample, and the absence of modification of the substrate indicates the absence of the microorganism in the sample. In particular, the substrate can consist of labeled peptide that is cleaved by a protease enzyme to give a signal that can be detected. Furthermore, this peptide can be designed with a particular sequence of amino acid residues extending from one end of the original substrate peptide as a "tag" for use in covalently coupling the substrate to a surface.

In another aspect, the present invention features a method for diagnosing the presence or absence of an infection in a subject, comprising the steps of a) contacting a sample obtained from a wound in a subject with a detectably labeled substrate for an enzyme produced and/or secreted by a microorganism, for example, *E. coli*, under conditions that result in modification of the substrate by the enzyme; and b) detecting a modification or the absence of a modification of the substrate. Modification of the substrate indicates the presence of an infection in the subject, and the absence of modification of the substrate indicates the absence of an infection in the subject.

In yet another aspect, the present invention features a method for diagnosing the presence or absence of a wound infection in a subject, comprising the steps of a) contacting a subject with a detectably labeled substrate for an enzyme produced and/or secreted by a microorganism, for example, *E. coli*, under conditions that result in modification of the substrate by the enzyme; and b) detecting a modification or the absence of a modification of the substrate. Modification of the substrate indicates the presence of a wound infection in the subject, and the absence of modification of the substrate indicates the absence of a wound infection in the subject.

In another aspect, the invention features a biosensor for detecting the presence or absence of a microorganism, for example, *E. coli*, comprising a solid support and a detectably labeled substrate for an enzyme produced and/or secreted by the microorganism, wherein the substrate is attached to the solid support.

In still another aspect, the present invention features a kit for detecting an infection, comprising a biosensor for detecting the presence or absence of a microorganism in a sample, and one or more reagents for detecting the presence of the microorganism that is the causative agent of the infection. For example, the reagent can be used to detect an enzyme secreted by the microorganism. In particular, the reagent can be used to detect the modification of the substrate of the biosensor.

DETAILED DESCRIPTION OF THE INVENTION

Figure 1:
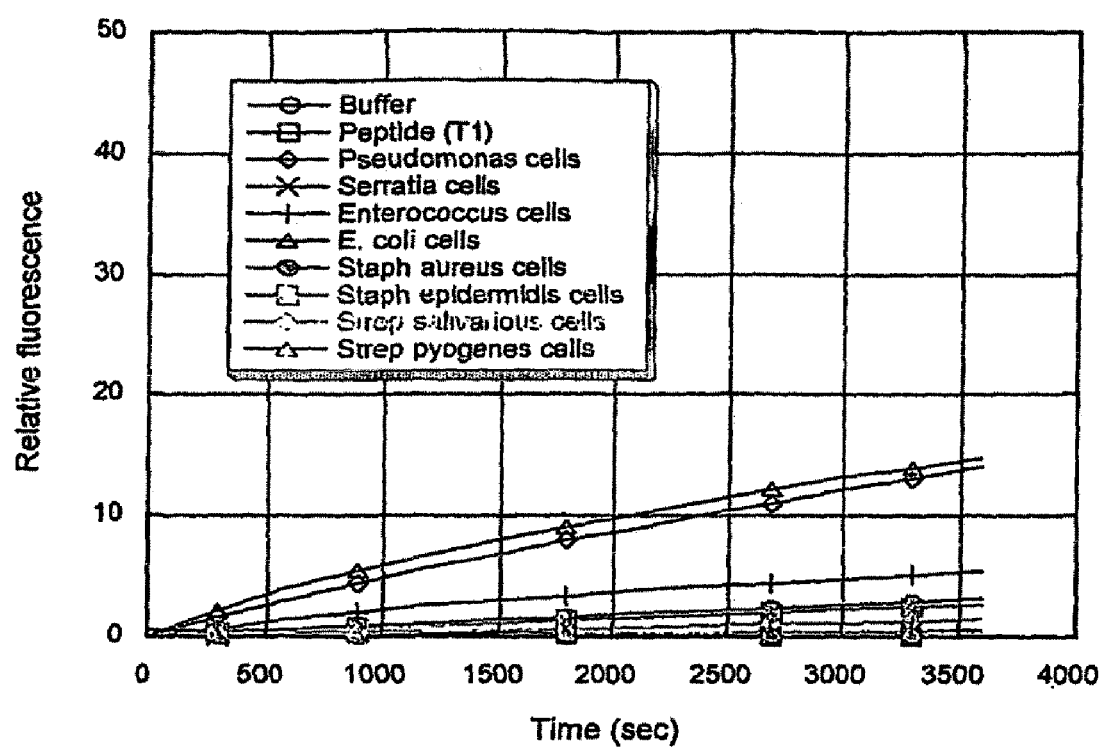
FIG. 1 is a graph of the cleavage of target substrate ecot1 (T1) (relative fluorescence) in samples containing various bacteria, as indicated. All bacterial samples are directly from culture and include cells and media. (Legend abbreviations: Buffer=20 mM tris buffer (pH 7.4) with 150 mM NaCl, Peptide T1=labeled peptide substrate)

As part of their normal growth processes, many microorganisms secrete a number of enzymes into their growth environment. These enzymes have numerous functions including, but not limited to, the release of nutrients, protection against host defenses, cell envelope synthesis (in bacteria) and/or maintenance, and others as yet undetermined. Many microorganisms also produce enzymes on their cell surface that are exposed to (and interact with) the extracellular environment. Many of these enzymes are specific to the microorganism that secretes them, and as such, can serve as specific markers for the presence of those microorganisms. A system that can detect the presence of these enzymes that are produced and/or secreted can equally serve to indicate the presence of the producing/secreting microorganism. Alternatively, a system that can detect the absence of these enzymes that are produced and/or secreted can equally serve to indicate the absence of the producing/secreting microorganism. Such a detection system is useful for detecting or diagnosing an infection. As used herein, an "infection" means a disorder caused by exposure to a pathogenic microorganism. In one example, the microorganism is *E. coli.* In another example, the disorder is a wound infection, an intestinal disorder, food poisoning, a kidney disorder, or a urinary tract infection.

A microorganism detection test system, as described herein can be tailored to detect one specific microorganism, for example, *E. coli* by identifying a protein such as a secreted enzyme specific to the microorganism to be detected. Alternatively, a test system can be designed to simultaneously identify more than one microorganism species (for example, at least 2, at least 5, or at least 10 different microorganism species), such as those that commonly cause infections. Identifying those enzymes that are common to certain classes of pathogenic microorganisms, but which are not present in non-pathogenic microorganisms is one way to achieve this goal. Such enzymes can be identified, for example, with a computer based bioinformatics screen of the microbial genomic databases. By using enzymes as the basis for detection systems, sensitive tests can be designed, since even a very small amount of enzyme can catalyze the turnover of a substantial amount of substrate.

The present invention pertains to the identification of bacterial proteins that are specific for microorganisms that are the causative agent of an infection. The presence of a pathogenic bacterium can be detected by designing a synthetic substrate that will specifically react with an enzyme that is present on the surface of the cell or secreted. These synthetic substrates can be labeled with a detectable label such that under conditions wherein their respective enzymes specifically react with them, they undergo a modification, for example, a visible color change that is observed.

The enzymes that are used in the bacteria detection method of the present invention are preferably infection-specific enzymes. As used herein, an infection-specific enzyme is an enzyme produced and/or secreted by a pathogenic bacteria, but is not produced and/or secreted by a non-pathogenic bacteria. Examples of pathogenic bacteria include, but are not limited to *staphylococcus* (for example, *Staphylococcus aureus, Staphylococcus epidermidis,* or *Staphylococcus saprophyticus*), *streptococcus* (for example, *Streptococcus pyogenes, Streptococcus pneumoniae,* or *Streptococcus agalactiae*), *enterococcus* (for example, *Enterococcus faecalis,* or *Enterococcus faecium*), *corynebacteria* species (for example, *Corynebacterium diptheriae*), *bacillus* (for example, *Bacillus anthracis*), *listeria* (for example, *Listeria monocytogenes*), *Clostridium* species (for example, *Clostridium perfringens, Clostridium tetanus, Clostridium botulinum, Clostridium difficile*), *Neisseria* species (for example, *Neisseria meningitidis,* or *Neisseria gonorrhoeae*), *E. coli, Shigella* species, *Salmonella* species, *Yersinia* species (for example, *Yersinia pestis, Yersinia pseudotuberculosis,* or *Yersinia enterocolitica*), *Vibrio cholerae, Campylobacter* species (for example, *Campylobacter jejuni* or *Campylobacter fetus*), *Helicobacter pylori,* pseudomonas (for example, *Pseudomonas aeruginosa* or *Pseudomonas mallei*), *Haemophilus influenzae, Bordetella pertussis, Mycoplasma pneumoniae, Ureaplasrna urealyticum, Legionella pneumophila, Treponema pallidum, Leptospira interrogans, Borrelia burgdorferi,* mycobacteria (for example, *Mycobacterium tuberculosis*), *Mycobacterium leprae, Actinomyces* species, *Nocardia* species, chlamydia (for example, *Chlamydia psittaci, Chlamydia trachomatis,* or *Chlamydia pneumoniae*), *Rickettsia* (for example, *Rickettsia* ricketsii, *Rickettsia prowazekii* or *Rickettsia* akar:), brucella (for example, *Brucella abortus, Brucella melitensis,* or *Brucella suis*), *Proteus mirabilis, Serratia marcescens, Enterobacter clocae, Acetinobacter anitratus, Klebsiella pneumoniae* and *Francisella tularensis.* Preferably, the infection-specific bacteria is *staphylococcus, streptococcus, enterococcus, bacillus, Clostridium* species, *E. coli, yersinia, pseudomonas, Proteus mirabilis, Serratia marcescens, Enterobacter clocae, Acetinobacter anitratus, *Klebsiella pneumoniae* or *Mycobacterium leprae*. For example, the infection-specific enzyme can be produced and/or secreted by *Staphylococcus aureus, Staphylococcus epidermidis, Streptococcus pyogenes, Pseudomonas aeruginosa, Enterococcus faecalis, Proteus mirabilis, Serratia marcescens, Enterobacter clocae, Acetinobacter anitratus, Klebsiella pneumoniae* and/or *Escherichia coli*.

Preferably, the enzyme is one or more of the following: phospholipase A protein, outer membrane protein T (ompT), or other omp proteins. The sequences of these proteins can be obtained by carrying out searches on protein sequence databases, for example, GenBank, and one skilled in the art can carry out such a search. Gene encoding such proteins can also be cloned using cloning techniques known to one of skill in the art.

Substrates for use in the present invention include any molecule, either synthetic or naturally-occurring that can interact with an enzyme of the present invention. Examples of substrates include those substrates described herein, as well as substrates for these enzymes that are known in the art. Other examples of substrates include ecot1(T1) derived fluorescent peptides, for example, Edans-DSRPVR-RRRRPRVSK-Dabcyl (SEQ ID NO: 1) or ecot2 (T2) derived fluorescent peptides, for example, Edans-KVSRRRRRGGD-Dabcyl (SEQ NO: 2), which can be cleaved by the ompT protein of pathogenic *E. coli*. Such substrates described herein can be obtained from commercial sources, e.g., Sigma (St. Louis, Mo.), or can be produced, e.g., isolated or purified, or synthesized using methods known to those of skill in the art.

The enzymes of the present invention can modify substrates, for example, proteins or polypeptides by cleavage, and such modification can be detected to determine the presence or absence of a pathogen in a sample. One method for detecting modification of a substrate by an enzyme is to label the substrate with two different dyes, where one serves to quench the fluorescence of the other dye by fluorescence resonance energy transfer (FRET) when the molecules, for example, dyes or colorimetric substances are in close proximity, and is measured by detecting changes in fluorescence.

FRET is the process of a distance dependent excited state interaction in which the emission of one fluorescent molecule is coupled to the excitation of another. A typical acceptor and donor pair for resonance energy transfer consists of 4-[[-(dimethylamino)phenyl]azo]benzoic acid (Dabcyl) and 5-[(2-aminoethylamino]naphthalene sulfonic acid (Edans). Edans is excited by illumination with 336 nm light, and emits a photon with wavelength 490 nm. If a Dabcyl moiety is located within 20 angstroms of the Edans, this photon will be efficiently absorbed. Dabcyl and Edans will be attached to opposite ends of a peptide substrate. If the substrate is intact, FRET will be very efficient. If the peptide has been cleaved by an enzyme, the two dyes will no longer be in close proximity and FRET will be inefficient. The cleavage reaction can be followed by observing either a decrease in Dabcyl fluorescence or an increase in Edans fluorescence (loss of quenching).

If the substrate to be modified is a protein, peptide, or polypeptide, the substrate can be produced using standard recombinant protein techniques (see for example, Ausubel et al, "Current Protocols in Molecular Biology," John Wiley & Sons, (1998), the entire teachings of which are incorporated by reference herein). In addition, the enzymes of the present invention can also be generated using recombinant techniques. Through an ample supply of enzyme or its substrate, the exact site of modification can be determined, and a more specific substrate of the enzyme can be defined, if so desired. This substrate can also be used to assay for the presence of the pathogenic bacteria.

The substrates are labeled with a detectable label that is used to monitor interactions between the enzyme and the substrate and detect any substrate modifications, for example, cleavage of the substrate or label resulting from such interactions. Examples of detectable labels include various dyes that can be incorporated into substrates, for example, those described herein, spin labels, antigen or epitope tags, haptens, enzyme labels, prosthetic groups, fluorescent materials, chemiluminescent materials, bioluminescent materials, and radioactive materials. Examples of suitable enzyme labels include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a chemiluminescent material includes luminol; examples of bioluminescent materials include luciferase, luciferin, and aequorin, and examples of suitable radioactive material include $^{125}I$, $^{131}I$, $^{35}S$, and $^{3}H$. Other examples of detectable labels include Bodipy, Pyrene, Texas Red, Edans, Dansyl Aziridine, IATR and fluorescein. Succimidyl esters, isothiocyanates, and iodoacetamides of these labels are also commercially available. When detectable labels are not employed, enzymatic activity can be determined by other suitable methods, for example, detection of substrate cleavge through electrophoretic analysis, or other methods known to one skilled in the art.

One example of a preferred detectable label is a chromogenic dye that allows monitoring of the hydrolysis of the substrate by the microorganism. An example of such a dye is para-nitrophenol. When conjugated to a substrate molecule, this dye will remain colorless until the substrate is modified by the secreted enzyme, at which point it turns yellow. The progress of the enzyme-substrate interaction can be monitored by measuring absorbance at 415 nm in a spectrophotometer. Other dyes that produce detectable modification, e.g., a visible color change, are known to those of skill in the art.

The sample in which the presence or absence of a bacteria, such as *E. coli* is detected, or an infection is diagnosed, can be, for example, a wound, a body fluid, such as blood, urine, sputum, or wound fluid (for example, pus produced at a wound site). The sample can also be any article that bacteria may be contained on/in, for example, a wound dressing, a catheter, a urine collection bag, a blood collection bag, a plasma collection bag, a disk, a scope, a filter, a lens, foam, cloth, paper, a suture, swab, test tube, a well of a microplate, contact lens solutions, food packaging material, or a swab from an area of a room or building, for example, an examination room or operating room of a healthcare facility, a bathroom, a kitchen, or a process or manufacturing facility.

The present invention also features a biosensor for detecting a (one or more, for example, at least 2, at least 5, at least 10, at least 20, at least 30, at least 50, at least 75, or at least 100) marker protein enzyme(s) described herein and for notifying a consumer of the presence of the marker protein. A biosensor for use in healthcare settings or home-use to detect infections comprising a (one or more) specific substrate(s) that is coupled to a solid support that is proximal to a wound or other body fluid that is being monitored for bacterial contamination is provided. Preferably, the substrate is covalently bound to a label and thus has a detection signal that upon proteolysis of the substrate-label bond indicates the presence of the bacteria. Such a biosensor can also be used in food preparation settings to detect for products that are contaminated with bacteria.

The biosensor is made by first determining the specific substrate of a specific enzyme characteristic of the bacteria to be detected. The determined specific substrate is labeled with one or more, and preferably, a plurality of detectable labels, for example, chromatogenic or fluorescent leaving groups. Most preferably, the labeling group provides a latent signal that is activated only when the signal is proteolytically detached from the substrate. Chromatogenic leaving groups include, for example, para-nitroanalide groups. Should the substrate come into contact with an enzyme secreted into a wound or other body fluid by bacteria or presented on the surface of a bacterial cell, the enzyme modifies the substrates in a manner that results in detection of such a modification, for example, a change in absorbance, which can be detected visually as a change in color (for example, on the solid support, such as a wound dressing), or using spectrophotometric techniques standard in the art.

The biosensor of the present invention also can comprise one or more substrates (for example, at least 2, at least 5, at least 10, at least 20, at least 30, at least 50, at least 75, or at least 100 substrates) for produced and/or secreted enzymes of pathogenic bacteria. The biosensor is a solid support, for example, a wound dressing (such as a bandage, or gauze), any material that needs to be sterile or free of microbial contamination, for example, a polymer, disk, scope, filter, lens, foam, cloth, paper, or sutures, or an article that contains or collects the sample (such as a urine collection bag, blood or plasma collection bag, test tube, catheter, swab, or well of a microplate).

Typically, the solid support is made from materials suitable for sterilization if the support directly contacts the wound or infected area or sample. In one embodiment of the present invention, the biosensor can be directly contacted with the wound or infected area. In some instances, a sterile covering or layer is used to prevent contamination of the wound or body fluid upon such direct contact. If such sterile coverings are used, they will have properties that make them suitable for sterilization, yet do not interfere with the enzyme/substrate interaction. Preferably, the portion of the biosensor that comes into contact with the wound is also nonadherent to permit easy removal of the biosensor from the sample surface. For example, if the biosensor comprises a wound dressing, the dressing contacts the wound for a time sufficient for the enzyme substrate to react and then the dressing is removed from the wound without causing further damage to the wound or surrounding tissue.

Substrates suitably labeled with detectable labels, for example, a chromogenic dye, and attached or incorporated into a sensor apparatus, can act as indicators of the presence or absence of pathogenic bacteria that secrete the aforementioned enzymes. When more than one substrate is utilized, each may be labeled so as to distinguish it from another (for example, using different detectable labels) and/or each may be localized in a particular region on the solid support.

Substrates with hydrophobic leaving groups can be non-covalently bound to hydrophobic surfaces. Alternatively hydrophilic or hydrophobic substrates can be coupled to surfaces by disulfide or primary amine, carboxyl or hydroxyl groups. Methods for coupling substrates to a solid support are known in the art. For example, fluorescent and chromogenic substrates can be coupled to solid substrates using non-essential reactive termini such as free amines, carboxylic acids or SH groups that do not effect the reaction with the pathogens. Free amines can be coupled to carboxyl groups on the substrate using, for example, a 10 fold molar excess of either N-ethyl-N'-(3-dimethylaminopropyl)carbodiimide hydrochloride (EDC) or N-cyclohexyl-N'-2-(4'-methyl-morpholinium) ethyl carbodiimide-p-toluene sulphonate (CMC) for 2 hrs at 4° C. in distilled water adjusted to pH 4.5 to stimulate the condensation reaction to form a peptide linkage. SH groups can be reduced with DTT or TCEP and then coupled to a free amino group on a surface with N-e-Maleimidocaproic acid (EMCA, Griffith et al., FEBS Lett. 134:261-263, 1981). Example of substrates are provided herein.

The polypeptides of the invention also encompass fragments and sequence variants of the polypeptide substrates described herein. Variants include a substantially homologous polypeptide encoded by the same genetic locus in an organism, i.e., an allelic variant, as well as other variants. Variants also encompass polypeptides derived from other genetic loci in an organism, but having substantial homology to a polypeptide substrate described herein Variants also include polypeptides substantially homologous or identical to these polypeptides but derived from another organism, i.e., an ortholog. Variants also include polypeptides that are substantially homologous or identical to these polypeptides that are produced by chemical synthesis. Variants also include polypeptides that are substantially homologous or identical to these polypeptides that are produced by recombinant methods.

The percent identity of two amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions×100). In certain embodiments, the length of the amino acid sequence aligned for comparison purposes is at least 30%, preferably, at least 40%, more preferably, at least 60%, and even more preferably, at least 70%, 80%, 90%, or 100% of the length of the reference sequence. The actual comparison of the two sequences can be accomplished by well-known methods, for example, using a mathematical algorithm. A preferred, non-limiting example of such a mathematical algorithm is described in Karlin et al., Proc. Natl. Acad. Sci. USA, 90:5873-5877, 1993). Such an algorithm is incorporated into the BLAST programs (version 2.2) as described in Schaffer et al. (Nucleic Acids Res., 29:2994-3005, 2001). When utilizing BLAST and Gapped BLAST programs, the default parameters of the respective programs can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

In another embodiment, the percent identity between two amino acid sequences can be accomplished using the GAP program in the GCG software package (Accelrys Inc., San Diego, Calif.) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (Accelrys Inc.), using a gap weight of 50 and a length weight of 3.

Other preferred sequence comparison methods are described herein.

The invention also encompasses polypeptides having a lower degree of identity but having sufficient similarity so as to perform one or more of the same functions performed by the polypeptide, e.g., the ability to act as a substrate for an *E. coli* specific protease. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Be; interchange of the hydroxyl residues Ser and Thr; exchange of the acidic residues Asp and Glu; substitution between the amide residues Mn and Gln; exchange of the basic residues Lys and Arg; and replacements among the aromatic residues Phe and Tyr. Guidance concerning which amino acid changes are likely to be phenotypically silent are found in Bowie et al., Science 247: 1306-1310, 1990).

Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region, such critical regions include the proteolytic cleavage site for an infection-specific protease.

Amino acids in a polypeptide of the present invention that are essential for cleavage by an *E. coli* specific protease can be identified by methods known in the art, such as site-directed mutagenesis or alanine-scanning mutagenesis (Cunningham et al., Science, 244: 1081-1085, 1989). The latter procedure introduces a single alanine mutation at each of the residues in the molecule (one mutation per molecule).

The invention also includes polypeptide fragments of the peptide substrates or functional variants thereof. The present invention also encompasses fragments of the variants of the polypeptides described herein. Useful fragments include those that retain the ability to act as substrates for an infection-specific protease.

Fragments can be discrete (not fused to other amino acids or polypeptides) or can be within a larger polypeptide. Further, several fragments can be comprised within a single larger polypeptide. In one embodiment a fragment desired for expression in a host can have heterologous pre- and pro-polypeptide regions fused to the amino terminus of the polypeptide fragment and an additional region fused to the carboxyl terminus of the fragment.

The biosensors of the present invention can be used in any situation where it is desirable to detect the presence or absence of bacteria, and in particular, pathogenic bacteria. For example, bacteria that collects on work surfaces in food manufacturing or food preparation facilities, or health care facilities, and in particular in operating rooms can be detected with a biosensor as described herein. A substrate, or more than one substrate, that can be modified by an enzyme secreted by or presented on the surface of a bacteria is labeled and covalently bound to a collector substrate, such as cotton fibers on the tip of a swab. When more than one substrate is utilized, each may be labeled so as to distinguish it from another (for example, using different detectable labels) and/ or each may be localized in a particular region on the solid support. The swab tip is used to wipe the surface suspected of being contaminated by bacteria. The swab tip is placed in a medium and incubated using conditions that allow modification of the labeled substrate if an enzyme specific for the bound, labeled substrate(s) is present.

The present invention also features a kit for detecting infection-specific bacteria as described herein. The kit can comprise a solid support, for example, having a plurality of wells (e.g., a microliter plate), to which a detectably labeled substrate is linked, coupled, or attached. A means for providing one or more buffer solutions is provided. A negative control and/or a positive control can also be provided. Suitable controls can easily be derived by one of skill in the art. A sample suspected of being contaminated by a pathogen described herein is prepared using the buffer solution(s). An aliquot of the sample, negative control, positive control is placed in its own well and allowed to react Those wells where modification of the substrate, for example, a color change is observed are determined to contain a microbial pathogen. Such a kit is particularly useful for detecting an infection in a subject.

Also encompassed by the present invention is a kit that comprises a biosensor, such as a packaged sterilized wound dressing or a sensor for food packaging material, and any additional reagents necessary to perform the detection assay.

A method for developing an assay for detecting a pathogenic bacteria that produces at least one enzyme that is secreted by the cell or present on the surface of the cell and a method for using the assay to detect pathogenic bacteria producing the enzyme(s) now follows:

Step 1) Define an amino acid sequence that uniquely identifies the prokaryotic microorganism of interest. Alternatively a (one or more) amino acid sequence that is unique to a specific group of pathogens, for example, infection-specific pathogens can be determined.

Select an amino acid sequence, for example, a protein, peptide, or polypeptide (marker sequence) that uniquely characterizes or marks the presence of the microorganism or group of microorganisms (for example, infection-specific pathogens) of interest. The selection can be performed utilizing a bioinfomatic approach, for example, as described in detail below. One or more amino acid sequences that are unique to a specific prokaryotic microorganism are determined.

Step 2) Obtain sufficient enzyme to determine conditions facilitating optimal modification of a substrate by the enzyme.

Isolate the enzyme from the extracellular medium in which the pathogenic bacteria to be assayed is growing, or from the cell membrane of the bacteria, using standard protein purification techniques, described, for example, in Ausubel (supra).

Alternatively, if the genetic sequence encoding the enzyme or the location of the genetic sequence encoding the enzyme are unknown, isolate and clone the genetic sequence encoding the marker amino acid of Step 1, or, first determine the genetic sequence, and then proceed as before.

Step 3) Determine the conditions for growth of the prokaryotic organism and for the production of an enzyme presented on the surface of the cell or secreted by the cell.

Determine medium required for growth of the specific prokaryotic microorganism of interest and for expression of its unique active enzyme into the medium. Also determine whether a second molecule, for example, an enzyme is required to convert the specific enzyme from an inactive precursor form to an active form. To determine if the enzyme has been secreted in an active form, a sample of the bacterial culture is provided with chosen potential substrates and cleavage of these substrates is determined. This can be done, for example, by combining the bacteria that produce the enzyme with the substrate in the appropriate media and incubating at 37° C. with gentle shaking. At preset times (0.1, 0.3, 1.0, 3.0, 5.0, 24 and 48 hours) the samples are centrifuged to spin down the bacteria, and a small aliquot is removed for an SDS-PAGE gel sample. After completion of the time course, the samples are run on a 10-15% gradient SDS-PAGE minigel. Then, the proteins are transferred to Immobilon Pseq (Transfer buffer, 10% CAPS, 10% methanol pH 11.0, 15 V for 30 minutes) using a Bio-Rad semi-dry transblotting apparatus. Following transfer of the proteins, the blot is stained with Coomassie blue R-250 (0.25% Coomassie Brilliant Blue R-250, 50% methanol, 10% acetic acid) and destained (high destine for 5 minutes, 50% methanol, 10% acetic acid; low destaine until complete, 10% methanol, 10% acetic acid) followed by sequencing from the N-terminal. Alternatively, the samples can be run on a mass spectrometer in order to map the sites of proteolytic cleavage using a Voyager Elite Mass spectrometer (Perceptive Biosystems, Albertville, Minn.).

Step 4) Identify any specific substrate(s) of the active enzyme protease. Examples of potential substrates include proteins, peptides, polypeptides, lipids, and peptidoglycan subunits. Label each substrate with a detectable label, for example, a detectable label described herein, or any other detectable label known in the art.

Step 5) Increase the specificity of the enzyme-substrate interaction (optional) by determining the active or binding site of the enzyme (for example, using FRET as described above), then determining the genetic sequence useful for producing the active or binding site, and cloning the determined genetic sequence to generate a more specific substrate.

Step 6) Provide a biosensor comprising one or more of the detectably labeled substrates identified above for detection of the protease of the pathogenic bacteria of interest.

The substrate can be attached to solid support, for example, a wound dressing, or an article that holds the enzyme and substrate, for example, a body fluid collection tube or bag, a microplate well, or a test tube. The solid support, if desired, can provide a plurality of derivatized binding sites for coupling to the substrate, for example, succimidyl ester labeled primary amine sites on derivatized plates (Xenobind plates, Xenopore, Hawthorne, N.J.).

Optionally, unoccupied reactive sites on the solid support are blocked by coupling bovine serum albumin, or the active domain of p26 thereto. p26 is an alpha-crystallin type protein that is used in this case to reduce non-specific protein aggregation. The ability of the p26 protein to refold heat denatured citrate synthetase before and after coupling to the surface of the food packaging is used as a control for determining p26 activity. Alpha-crystallin type proteins were recombinantly produced using standard recombinant DNA technologies (see Ausubel, supra). Briefly, the plasmid containing the beta sheet-charged core domain of p26 is electroporated into electrocompetent BL21(DE3) cells (Bio-Rad *E. coli* pulser). The cells are grown up to an $OD_{600}$ of 0.8, then induced with 1 mM IPTG for 4 hours. The cells are spun down, and sonicated in low buffer (10 mM Tris, pH 8.0, 500 mM NaCl, 50 mM Imidizole) to lyse (Virsonic, Virtis, Gardiner, N.Y.). The lysate is spun down at 13,000×g for 10 minutes, and the supernatant 0.45 and 0.2 μm filtered. This filtrate is loaded onto a Ni-NTA superose column (Qiagen, Valencia, Calif., cat #30410). High buffer (10 mM Tris pH 8.0, 500 mM NaCl, 250 mM Imidizole) is used to elute the protein.

Allow the enzyme(s) to come into contact with the substrate(s), and monitor the reaction for a modification in the detectably labeled substrate, as described herein. Modification of the substrate indicates that the enzyme produced/secreted by the bacteria is present in the reaction. In addition, the absence of modification of the substrate indicates that the enzyme is not present in the sample. If the bacteria or enzyme is from a wound or other infected area, modification of the substrate indicates that the bacteria is present in the wound or infected area, and that the wound or area is infected, while the absence of modification of the substrate indicates that the particular bacteria is not present in the wound or area, and that the wound or area is not infected with that particular bacteria.

EXAMPLES

The present invention will now be illustrated by the following Examples, which are not intended to be limiting in any way.

Example 1

Detection of the Presence of *E. coli* in a Sample

*E. coli* Assay Development

The Gram-negative bacterium *Escherichia coli* is the best characterized human pathogen and is known to secrete very few molecules unless specifically required for virulence. The virulent strains include those likely to cause food poisoning (O157:H7), intestinal disorders (EHECs) or urinary tract infections (UTIs). However, most strains of E, coli can harmlessly coexist with humans and are not likely to cause disease under normal circumstances.

Although many of the genes are common to other bacteria, *E. coli* has developed some unique means of coexistence. A search of the *E coli* K-12 genome by subtraction of several other pathogenic and non-pathogenic bacteria provides a list of genes that are unique to this organism. The listing obtained includes the outer membrane proteins phospholipase A, outer membrane protein T (ompT) and several other omp genes.

The gene ompT encodes an enzyme that is found on the outer surface of the cell membrane and is used to protect the cell from strongly cationic antimicrobial peptides (defensins) produced by humans. The protein OmpT is a membrane bound protease that has been shown to efficiently cleave protamines (salmon milt). The enzyme binds positively charged proteins and peptides and cleavage occurs preferentially at a site between two positively charged residues.

The peptide substrates used here were labeled with the fluorescent probe edans (5((2-aminoethyl)amino)naphthalene-1-sulfonic acid) and the quencher dye molecule dabcyl ((4-(4-(dimethylamino)phenyl)azo)benzoic acid). The labeled peptides ecot1 (T1) and ecot2 (T2) sequences used are as follows:

```
                                            (SEQ ID NO: 1)
    (T1) Edans - DSRPVRRRRRPRVSK - Dabcyl (SEQ ID NO: 2)
    (T2) Dabcyl - KVSRRRRRGGD - Edans
```

The bacteria were grown in an incubator overnight at 37° C. in 5 mL BHT (Brain Heart Infusion) media. Each of the resulting cultures was split into two samples. One was used as a culture, and the other was spun down by centrifugation and the supernatant was collected. The assays were run in 20 mM tris buffer (pH 7.4) with 150 mM NaCl added. The reaction was carried out with 5 μL of culture or supernatant and 5 μL of peptide substrate (10 mg/mL in water) in 100 μL total volume at 37° C. The reaction was followed on a fluorimetric plate reader using an excitation wavelength of 355 nm and an emission wavelength of 485 nm.

The first set of experiments was performed by addition of the bacterial culture directly into the assay solution. The protease OmpT is a membrane bound protein and would not be expected to be found secreted into the media. The first assay to be run used the peptide ecot1(T1) as substrate. The results are shown in FIG. 1.

As shown in FIG. 1, protease activity was observed for both *E. coli* and *Pseudomonas* with the T1 peptide substrate. The same protease assay was repeated under identical conditions for substrate ecot2 (T2). The results are shown in FIG. 2

Figure 2:
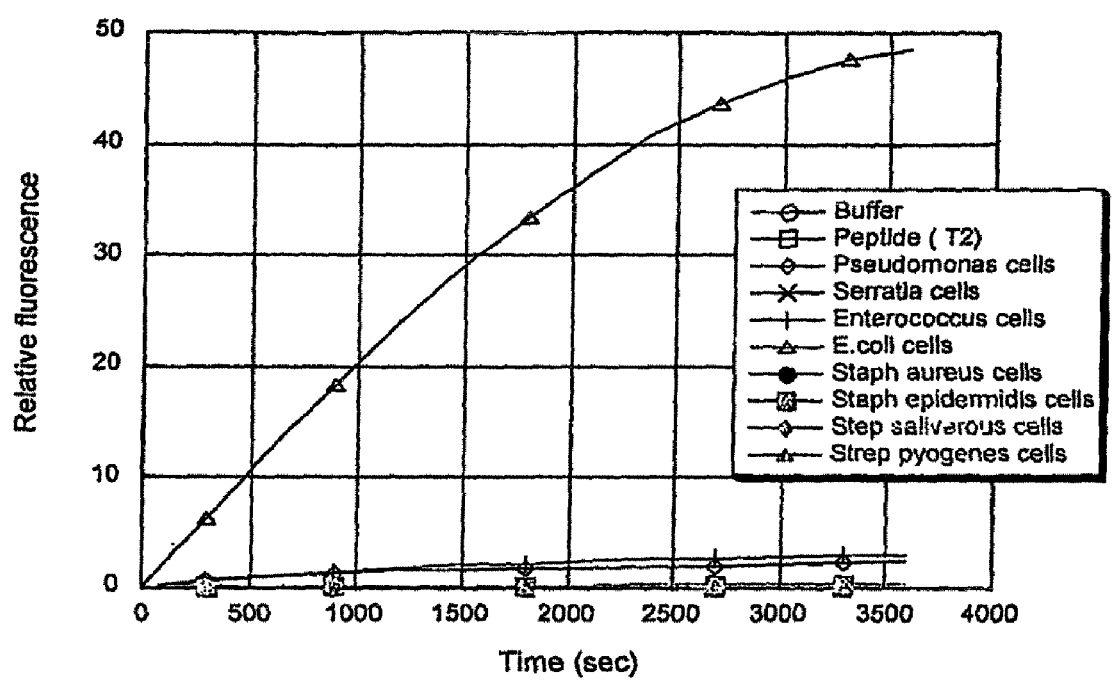
FIG. 2 is a graph of the cleavage of target substrate ecot2 (12) (relative fluorescence) in samples containing various bacteria, as indicated. All bacterial samples are directly from culture and include cells and media. (Legend abbreviations: Buffer=20 mM tris buffer (pH 7.4) with 150 mM NaCl, Peptide T2=labeled peptide substrate)

As shown in FIG. 2, the sample containing *E. coli* cells reacted with this substrate. This peptide appears to be both efficient and selective for *E. coli*.

To test whether the protease is membrane associated, as expected for *E. coli* OmpT, the protease assays were repeated with the supernatants obtained from each bacterial culture. When peptide substrate T1 was used with the bacterial culture supernatants, the protease activity observed for *Pseudomonas* was still present, but the activity associated with the *E. coli* cells was not present in the supernatant. This indicates that the protease from *Pseudomonas* is secreted into solution, but the *E. coli* protease observed here is membrane bound and may be due to OmpT. When peptide substrate T2 was used with the bacterial culture supernatants, the peptide substrate 12 did not show any reactivity with a secreted protease from *E. coli* or any of the other bacteria tested. This indicates that peptide T2 appears to be selective for the *E. coli* outer membrane protease OmpT.

Figure 3:
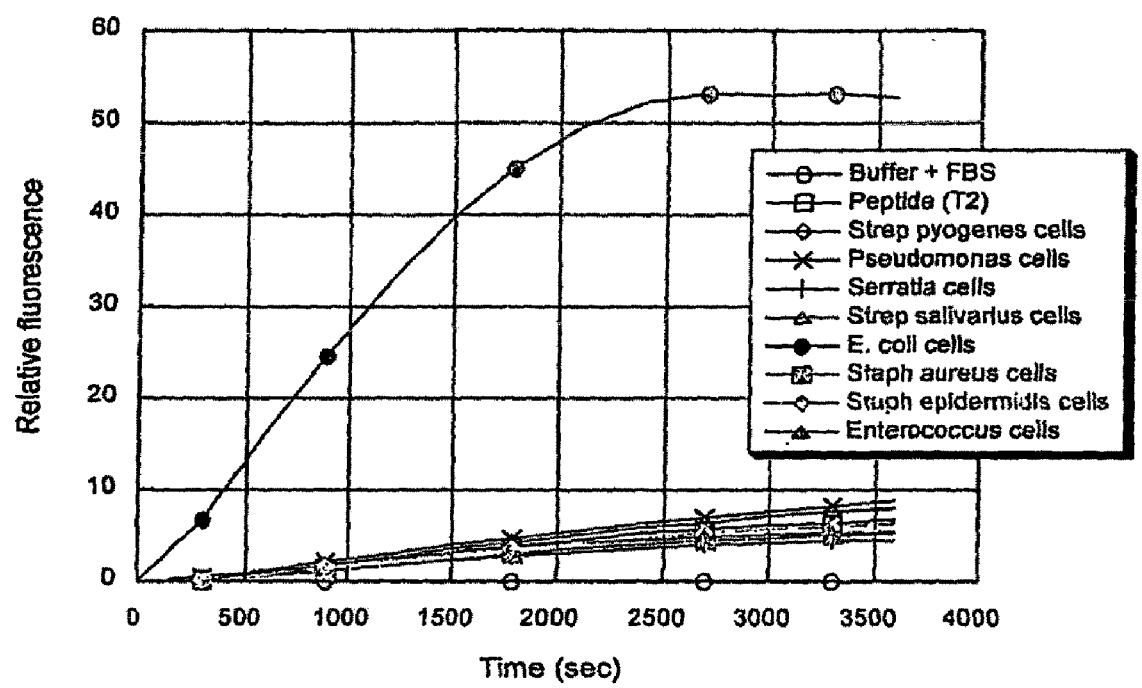
FIG. 3 is a graph of the cleavage of target substrate ecot2 (T2) (relative fluorescence) in samples containing various bacteria, as indicated, plus fetal bovine serum (FBS). All bacterial samples are directly from culture and include cells and edia. (Legend abbreviations: Buffer=20 mM tris buffer (pH 7.4) with 150 mM NaCl, Peptide 12=labeled peptide substrate, FBS=fetal bovine serum)

The 12 peptide substrate was further tested for cross reactivity with the types of conditions and molecules that may be present in a wound environment. A fluid that may be present in a wound, at least initially, is serum. In order to test for reactivity with serum the reaction buffer was modified to by addition 5% fetal bovine serum and the protease assay was repeated, using the 12 peptide substrate. The results are shown in FIG. 3. As shown in FIG. 3, detection of the presence of *E. coli* in the *E. coli* sample occurred in the presence of FBS.

Figure 4:
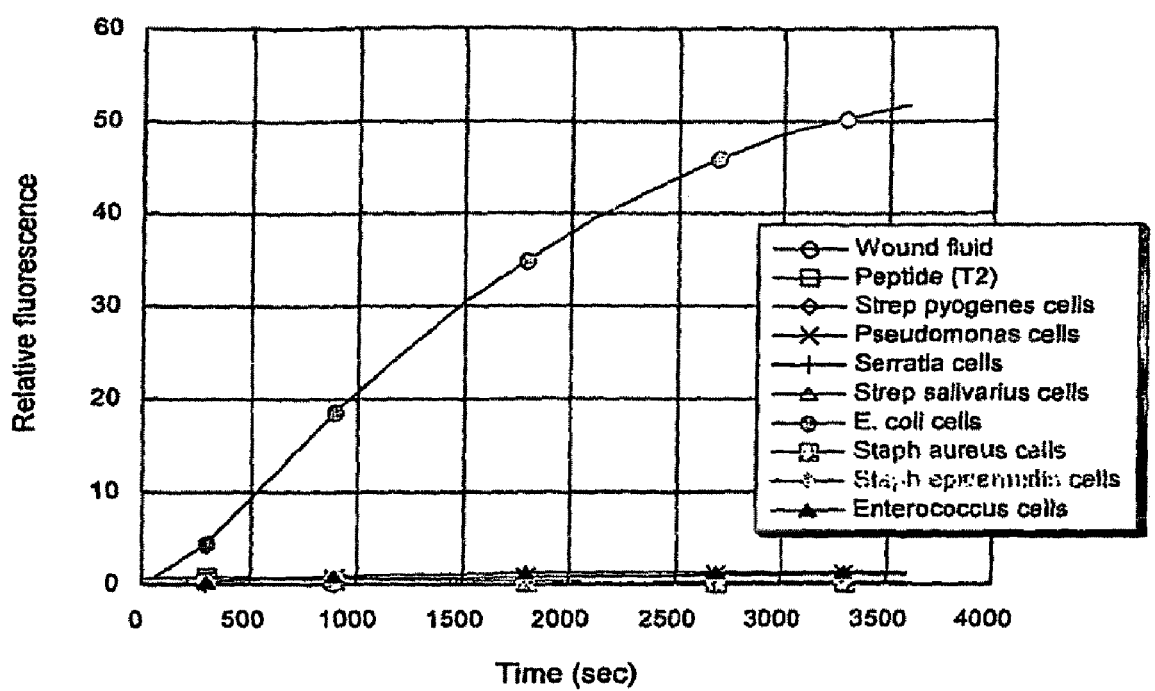
FIG. 4 is a graph of the cleavage of target substrate ecot2 (T2) (relative fluorescence) in simulated wound fluid samples containing various bacteria plus bovine serum albumin (BSA). All bacterial samples are directly from culture and include cells and media. (Legend abbreviations: Buffer=20 mM tris buffer (pH 7.4) with 150 mM NaCl, Peptide 12=labeled peptide substrate)

The protease assay was also tested in a simulated wound fluid buffer. The buffer was tris-buffered saline, as described above, to which 5% (by weight) bovine serum albumin was added. The protease assay was repeated, again using the 12 peptide substrate. The results of this assay are shown in FIG. 4. As shown in FIG. 4, the protease reactivity of the *E. coli* sample was not affected by the simulated wound fluid buffer. Under these conditions the peptide 12 appears to be a rapid and selective probe for the detection of *E. coli* cells.

Example 2

Development of Biosensor Surfaces

The attachment of molecules to surfaces can be performed by the use of several different types of interactions. Typically, proteins can be attached to surfaces using hydrophobic, electrostatic, or covalent interactions. There are many commercially available membranes and resins with a variety of surface properties. Surfaces can also be chemically modified to provide the required surface properties.

Commercially available transfer membranes exist for protein and peptide binding. They consist of positively and negatively charged polymers such as ion exchange membrane disc filters and resins. Nitrocellulose membranes offer hydrophobic and electrostatic interactions. Glass fiber membranes offer a hydrophobic surface that can easily be chemically modified to add functional groups. There are also modified polymer membranes that offer reactive functional groups that covalently bind proteins and peptides.

It is also possible to utilize various functional groups on membranes or resins and a crosslinking agent to covalently link to proteins. Crosslinking reagents contain two reactive groups thereby providing a means of covalently linking two target functional groups. The most common functional groups to target on proteins are amine, thiol, carboxylic acid, and alcohol groups that are used to form intramolecular crosslinks. Crosslinking agents can be homobifunctional or heterobifunctional and a selection of crosslinking agents of various lengths are commercially available.

Initially the peptides studied were designed as substrates for bacterial assay development using fluorescence energy transfer (Eclan and Dabcyl) for detection. T2, which is selective for *E. coli*, is an example of such a substrate, and is described herein.

In order to develop substrates specifically for surface immobilization, several versions of the T2 peptide were made. The peptides were designed to include lysine groups (amine functional group) at one end of the peptide in the case of T2. The addition of two lysine groups (KK) at one end of the peptide serve as a "tag" and provide ideal groups for attachment to surfaces through techniques such as electrostatic interactions or through covalent attachment. The peptide T4 was desired to include a cysteine group (C) and three histidine groups (HHH) at one end. The addition of a cysteine provides another ideal group or tag to perform covalent attachments through the thiol group. The inclusion of three histidine groups also provides the potential for attachment to nickel resins.

The peptide sequence for T2 was modified as shown:

```
                                            (SEQ ID NO: 2)
    T2      (dabcy1-K)VSRRRRGG(D-edans)

(SEQ ID NOS: 3 and 4)
    T3      KKAS(E-edans)VSRRRRGG(K-dabcy1)

(SEQ ID NOS: 5 and 6)
    T4      CHHHAS(E-edans)VSRRRRGG(K-dabcy1)
```

The pre-peptide tags were added to the original sequences to allow for attachment to a surface.

Figure 5:
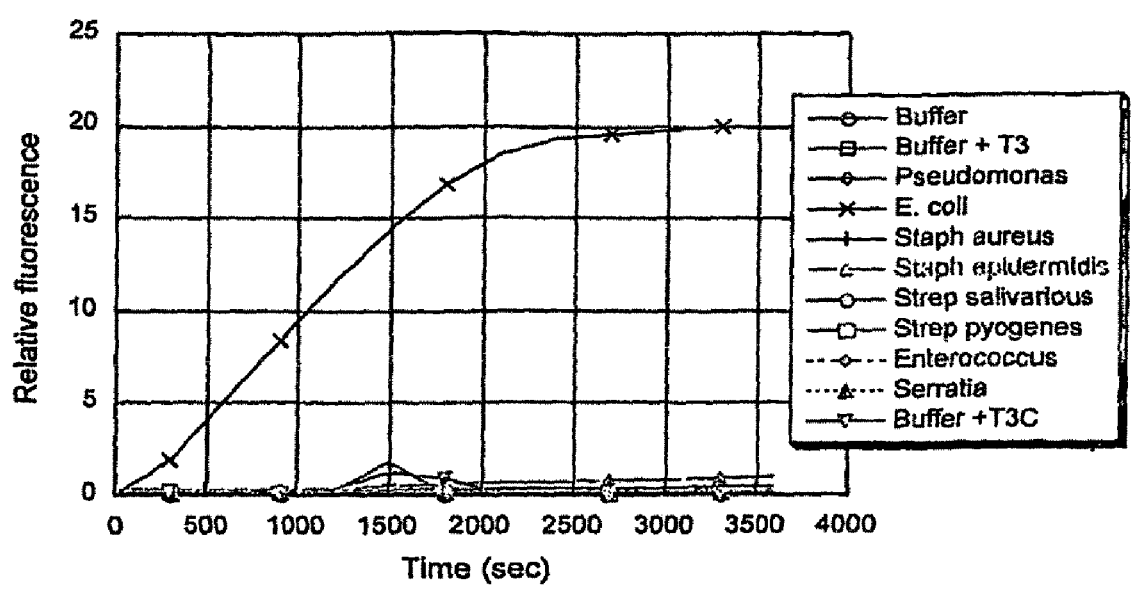
FIG. 5 is a graph of cleavage of protease substrate T3 (relative fluorescence) over time in samples containing buffer, buffer plus T3, buffer plus T3C (crude peptide), or culture including cells and media from *Pseudomonas, E. coli, S. aureus* (*Staph aureus*), *S. epidermidis* (*Staph epidermidis*), *S. Salivarius* (*Strep salivarius*), *S. pyogenes* (*Strep pyogenes*), *Enterococcus,* or *Serratia.*

The protease assay, described herein for detection of *E. colt* was run with the modified version of *T*2, T3. Bacteria (*Pseudomonas, E. coli, S. aureus, S. epidermidis, S. salivarius, S. pyogenes, Enterococcus,* and *Serratia*) were grown in an incubator overnight at 37° C. in 5 mL BHI (Brain Heart Infusion) media. The assays were run in 20 mM tris buffer (pH 7.4) with 150 mM NaCl added. The reaction was carried out with 7 μL of culture including cells and media and 3 peptide substrate (5 mg/mT, in water) in 100 μL total volume at 37° C. The reaction was followed on a fluorimetric plate reader using an excitation wavelength of 355 nm and an emission wavelength of 485 nm. The results are shown in FIG. 5. As shown in FIG. 5, this assay appears to be specific for *E. coli*.

Metal chelate (affinity binding) interactions can provide a stronger bond to biological molecules. A his-tag built into the peptide substrate, for example T4 can be used to allow linkage to a nickel binding resin. The resin is incubated with a suitable culture, for example, *E. coli* for 30 minutes at 37° C. After centrifugation the buffer is removed and the pelleted resin is imaged. The fluorescence produced by the peptide is then detected. In an example of such a detection assay, *E. coli* was detected using a biosensor in which a his-tagged T4 peptide was linked to a nickel binding resin and subsequently exposed to *E. coli* cultures or exposed to BHI media without bacteria.

Lysine peptide tags, for example, T3 can be used to link to a surface such as UltraBind™ (Pall Gelman Laboratory, Ann Arbor, Mich.). UltraBind is a polyethersulfone membrane that is modified with aldehyde groups for covalent binding of proteins. Proteins are directly reacted with the UltraBind surface. It is also possible to link proteins or peptides to the surface using cross linker chains. For example, the carborliimide, EDC (1-ethyl-3(3-dimethylaminopropyl)carbodiimide, hydrochloride) is commonly used to link carboxylic acid groups to amines. The linking of the peptide with a cross linking agent allows the choice of a linker chain to extend the peptide off the surface of the membrane while still covalently binding it. The linking of the peptide through a cross linker can be optimized to make the peptide available to the bacterial enzymes. This allows for optimization of the reaction time of the sensor since peptide availability is directly related to this parameter.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for detecting the possible presence or absence of pathogenic *Escherichia coli* bacteria in a sample, comprising the steps of:
   a) contacting the sample with a detectably labeled peptide substrate for a membrane-bound protease enzyme specific for pathogenic *Escherichia coli*, under conditions that result in cleavage of said substrate by said enzyme; and
   b) detecting the cleavage or the absence of cleavage of said peptide substrate, wherein cleavage of said substrate indicates the possible presence of pathogenic *Escherichia coli* bacteria in said sample, and wherein the absence of cleavage of said substrate indicates the absence of possible pathogenic *Escherichia coli* bacteria in said sample, and wherein said detectably labeled substrate specific for *Escherichia coli* is selected form the group consisting of:
   (dabcyl-K) VSRRRRRGG(D-edans) (SEQ ID NO:2)
   KKAS(E-edans)VSRRRRRGG(K-dabcyl) (SEQ ID NOS: 3 and 4),
   and
   CHHHAS(E-edans)VSRRRRRGG(K-dabcyl) (SEQ ID NOS: 5 and 6).

2. The method of claim 1, wherein said sample is selected from the group consisting of a fluid obtained from a wound on a subject and a body fluid.

3. The method of claim 1, wherein said substrate is on a solid support.

4. The method of claim 3, wherein said solid support comprises a material required to be free of microbial contaminants.

5. The method of claim 3, wherein said solid support is a wound dressing.

6. The method of claim 3, wherein said solid support is selected form the group consisting of a wound dressing, negatively and positively charged polymers, transfer membranes, nitrocellulose, a container for holding body fluids, a disk, a scope, a filter, a lines, foam, cloth, paper, a suture, a food packaging material, and a swab.

7. The method of claim 6, wherein said container for holding body fluids is selected from the group consisting of a urine collection bag, a blood collection bag, a plasma collection bag, a test tube, a catheter, and a well of a microplate.

* * * * *